(12) United States Patent
Veligdan

(10) Patent No.: US 6,673,065 B1
(45) Date of Patent: Jan. 6, 2004

(54) SLENDER TIP LASER SCALPEL

(75) Inventor: James T. Veligdan, Manorville, NY (US)

(73) Assignee: Brookhaven Science Associates, Upton, NY (US)

( * ) Notice: Subject to any disclaimer, the term of this patent is extended or adjusted under 35 U.S.C. 154(b) by 0 days.

(21) Appl. No.: 09/629,747

(22) Filed: Jul. 31, 2000

(51) Int. Cl.[7] ............................................. A61B 18/20
(52) U.S. Cl. ............................. 606/16; 606/13; 606/17
(58) Field of Search ......................... 606/10–17; 607/88, 607/89

(56) References Cited

U.S. PATENT DOCUMENTS

| | | | | |
|---|---|---|---|---|
| 4,273,127 A | * | 6/1981 | Auth et al. | ............... 219/121.6 |
| 4,676,242 A | * | 6/1987 | Doi | ............... 137/13 |
| 5,352,221 A | * | 10/1994 | Fumich | ............... 606/15 |
| 5,401,272 A | * | 3/1995 | Perkins | ............... 606/15 |
| 5,571,098 A | * | 11/1996 | Domankevitz et al. | ....... 606/15 |
| 5,658,275 A | * | 8/1997 | Saadat | ............... 606/15 |
| 5,702,360 A | * | 12/1997 | Dieras et al. | ............... 604/22 |
| 5,707,368 A | | 1/1998 | Cozean et al. | |
| 5,951,543 A | * | 9/1999 | Brauer | ............... 606/10 |
| 5,968,039 A | * | 10/1999 | Deutsch et al. | ............... 606/10 |
| 6,129,723 A | * | 10/2000 | Anderson et al. | ............... 606/10 |
| 6,294,757 B1 | * | 9/2001 | Whittenbury | ............... 219/121.72 |

\* cited by examiner

*Primary Examiner*—Roy D. Gibson
*Assistant Examiner*—Henry M. Johnson
(74) *Attorney, Agent, or Firm*—Reed Smith LLP; William J. McNichol, Jr.; Matthew J. Esserman

(57) ABSTRACT

A laser scalpel includes a ribbon optical waveguide extending therethrough and terminating at a slender optical cutting tip. A laser beam is emitted along the height of the cutting tip for cutting tissue therealong.

63 Claims, 3 Drawing Sheets

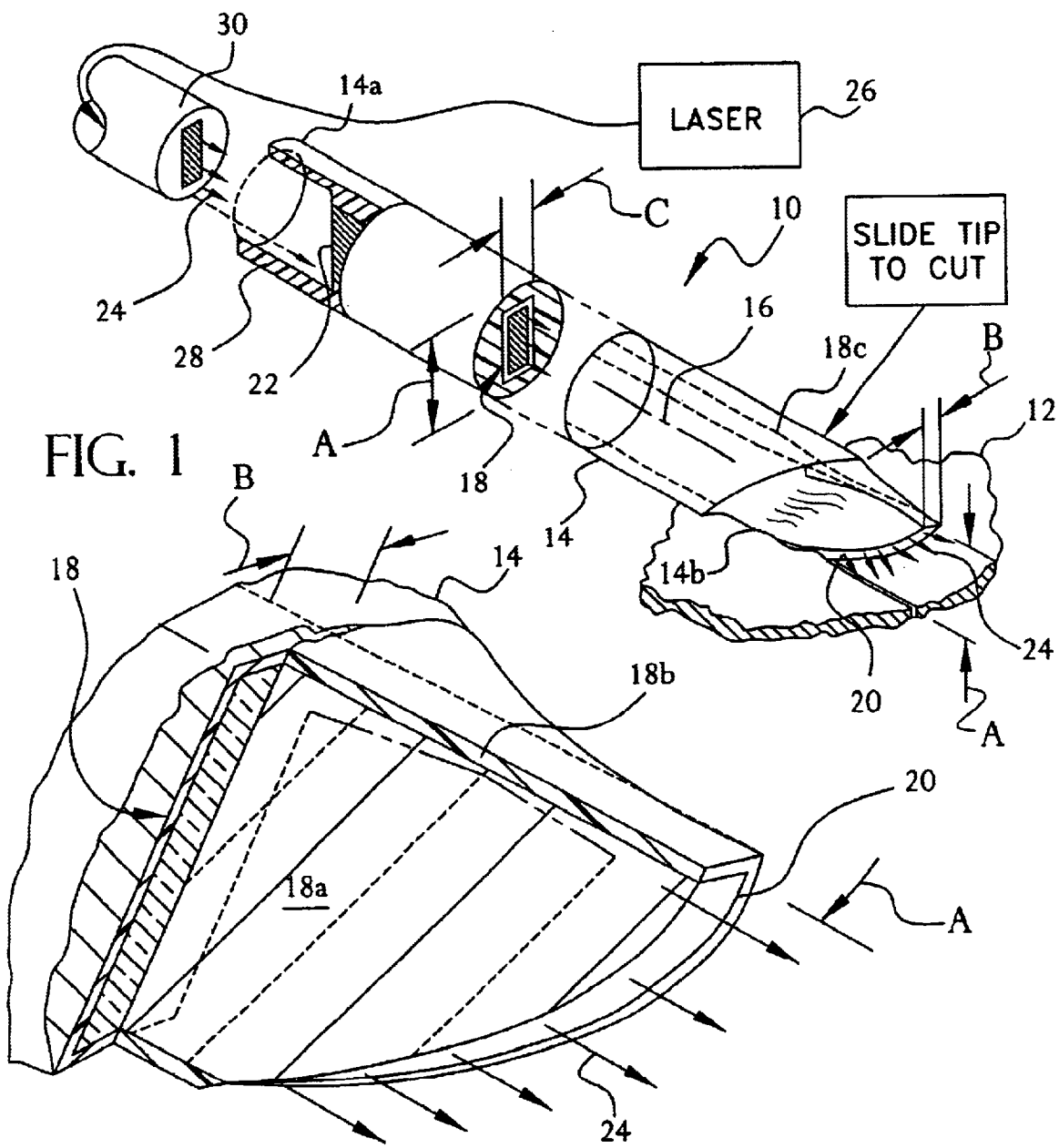

SLENDER TIP LASER SCALPEL

This invention was made with Government support under contract number DE-AC02-98CH10886, awarded by the U.S. Department of Energy. The Government has certain rights in the invention.

BACKGROUND OF THE INVENTION

The present invention relates generally to cutting instruments, and, more specifically, to laser scalpels.

A typical metal scalpel includes a razor sharp cutting edge or tip which permits a surgeon to cut various biological tissues for performing surgery on a patient. The scalpel is hand held and manually guided to cut where desired, and the depth of the cut is controlled in response to feeling and seeing the cut as it is made. The scalpel provides tactile feedback to the surgeon as the surgeon applies pressure through the scalpel during cutting, and the surgeon also views the cut being made at the tip of the scalpel.

Laser scalpels are being developed and introduced into surgery for various types of operations. In a typical laser scalpel, a laser beam is emitted from the scalpel tip and has a small focal spot of concentrated energy at a distance away from the scalpel tip which cuts biological tissue by local burning or vaporizing at the focal spot. The scalpel tip itself does not contact the tissue being cut.

Since the tip of the laser scalpel does not contact the tissue being cut, significant problems are created. Firstly, the surgeon obtains no tactile feedback from the scalpel, therefore, the surgeon cannot feel the nature or depth of the cut. Also, since the scalpel tip is suspended over the tissue, slight variation in the offset distance therebetween affects the depth of the laser cut. It is thusly difficult to control cutting depth which may be too deep or too shallow depending upon the variable offset distance between the scalpel tip and the tissue being cut.

Furthermore, since the laser scalpel merely cuts at a single point, the scalpel must be oscillated by the surgeon in a generally straight line for cutting along that line without concentrating the laser beam at any one point for an excessive amount of time.

Accordingly, it is desired to provide an improved laser scalpel more closely simulating the touch and feel of a conventional razor scalpel for providing tactile feedback to the surgeon and facilitating the ability to precisely cut along a line.

BRIEF SUMMARY OF THE INVENTION

A laser scalpel includes a ribbon optical waveguide extending therethrough and terminating at a slender optical cutting tip. A laser beam is emitted along the height of the cutting tip for cutting tissue therealong.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which:

FIG. 1 is a partly sectional, isometric view of a laser scalpel in a cutting system in accordance with an exemplary embodiment of the present invention.

FIG. 2 is an enlarged, partly sectional view of the cutting tip of the laser scalpel illustrated in FIG. 1.

DETAILED DESCRIPTION OF THE INVENTION

Figure 3:
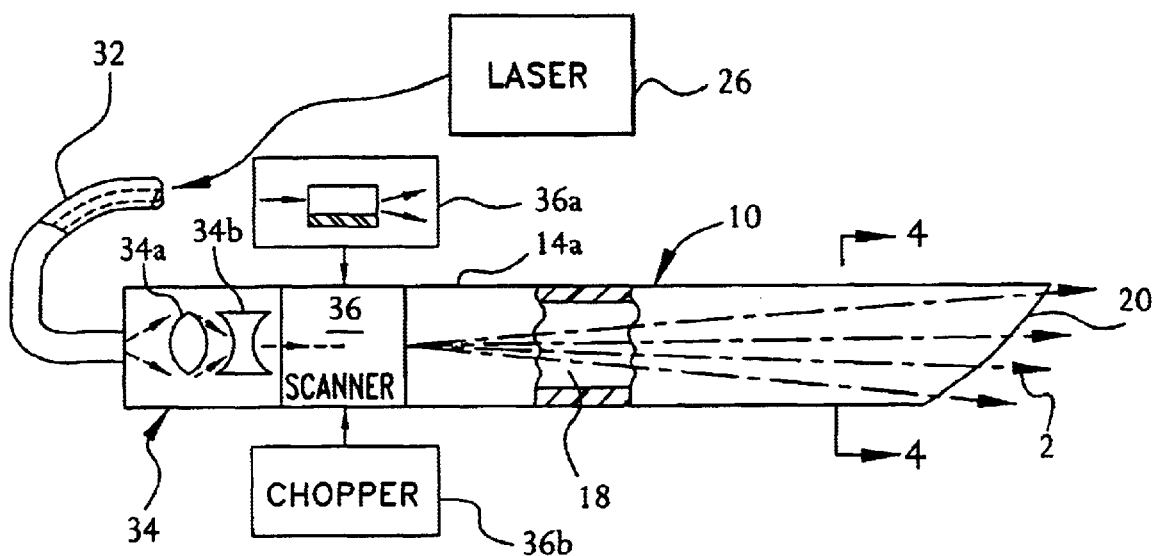
FIG. 3 is a schematic side view of a laser scalpel in accordance with another embodiment of the present invention.

Illustrated schematically in FIG. 1 is a laser knife or scalpel 10 in accordance with an exemplary embodiment of the present invention configured for cutting a surface 12 such as that found on living biological tissue of any type in a living human patient undergoing surgery. The scalpel includes an elongate barrel or shaft 14 which is preferably cylindrical and small in diameter for simulating a conventional razor scalpel of ergonomic form as desired.

The shaft includes a central longitudinal axis 16 extending between opposite proximal and distal ends 14a,b. Extending centrally through the shaft between its opposite ends is a flat or planar ribbon optical waveguide 18. The waveguide terminates at a correspondingly slender optical cutting tip 20 disposed at the distal end of the shaft. The cutting tip 20 is defined as the optical outlet of the waveguide at the shaft distal end, with the waveguide also including an inlet face 22 disposed at the shaft proximal end for receiving a laser beam 24 from a suitably powered laser 26 of any conventional form.

As shown in FIG. 2, the optical waveguide 18 includes a central core 18a surrounded on all sides by a suitable cladding 18b. The core is optically transparent or transmissive for channeling the laser beam 24 therethrough. The cladding 18b is provided in a thin layer around the core and has a refractive index less than that of the core for effecting substantially total internal reflection of the laser beam as it travels through the waveguide during operation.

The waveguide may be made of any suitable material, with the core being a polycarbonate for example with a refractive index of about 1.56, and the cladding being a suitable acrylic plastic for example with a refractive index of about 1.49. The waveguide may optionally be flexible. The shaft 14 integrally surrounds the waveguide and may be a suitable plastic or silicone for example for providing a comfortable and slip resistant surface for being hand-held by the surgeon.

Referring again to FIG. 1, the shaft 14 is relatively thin and elongate along the longitudinal axis 16, with the cutting tip 20 being relatively slender or narrow laterally or transversely to the longitudinal axis 16. In the preferred embodiment illustrated, the waveguide 18 has a planar rectangular cross section which extends to the tip 20, with the tip 20 having a height A occupying most of the diameter of the shaft, and a relatively narrow thickness or width B as measured transverse to the longitudinal axis 16.

For example, the waveguide at its cutting tip 20 may have a height A of about 5 mm and a width B of about 50 microns. In this way, the laser beam 24 may be channeled along the full height of the waveguide for emitting the laser beam along the full height of the cutting tip 20 for automatically cutting the surface 12 along a corresponding line instead of an individual spot.

As shown in FIG. 2, the laser beam 24 is emitted from the cutting tip 20 and since the optical waveguide is planar, the laser beam 24 is focused to have its maximum cutting or burning energy directly at the tip 20 itself. In this way, the tip may be directly placed against the surface of the tissue so that the emitted laser beam directly cuts the tissue at the outlet of the waveguide or the exit edge of the cutting tip 20. As the cutting tip is offset or spaced away from the tissue, the power density of the emitted laser quickly degrades and loses its cutting ability.

Figure 6:
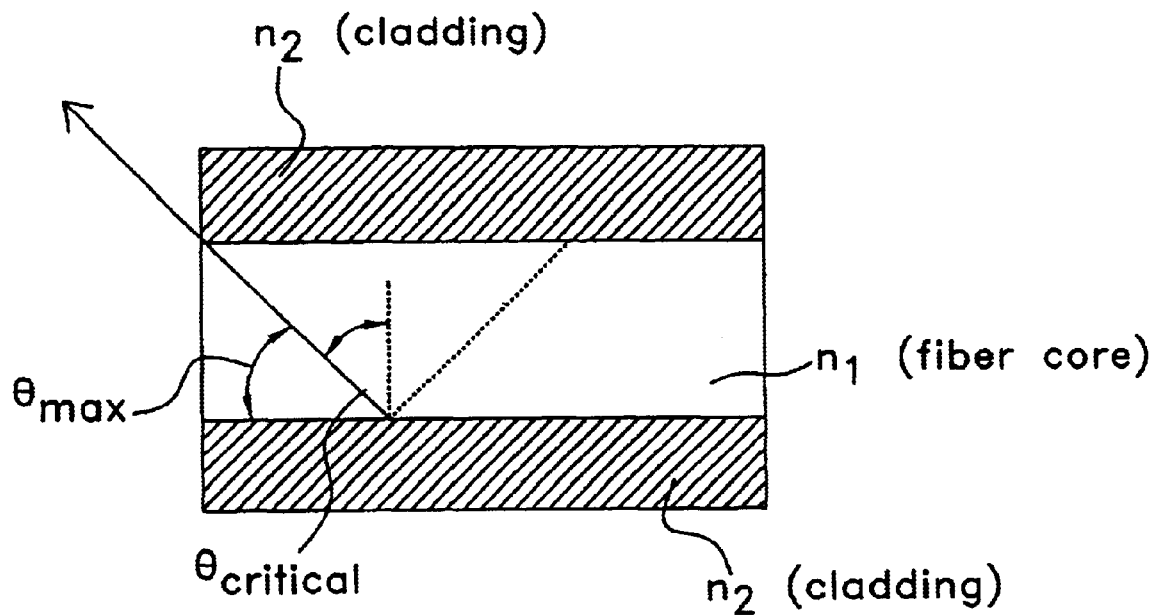
FIG. 6 is an enlarged, partly cross-sectional side view of the cutting tip of the laser scalpel illustrated in FIG. 1.

To achieve this cutting requirement, the range of intensity of light exiting the exit edge of the cutting tip 20 is carefully selected. In a worst case (i.e., least divergent) scenario, when the numerical aperture NA=0.2, $\Delta n=0.01$ (see FIG. 6), the exit angle $\theta_{max}$ of the exiting light rays is 12°. Therefore, the full spread angle at the exit edge is 24° ($2\times\theta_{max}$). With a 50 $\mu$m wide exit edge, the spot size is 50 $\mu$m when the exit edge is in contact with the tissue. If the distance between the exit edge and tissue is increased to 50 $\mu$m, the spot size becomes 70 $\mu$m. Since the area of the 50 $\mu$m spot is $1.96\times10^{-5}$ cm$^2$ and the area of 70 $\mu$m spot in $3.85\times10^{-5}$ cm$^2$, the power per unit area at a 70 $\mu$m spot is ½ of that at a 50 $\mu$m spot. With a 1 Watt laser focused to a 50 $\mu$m spot size, $P_{at\ tip}=50,000$ Watts/cm$^2$ which is sufficient to cut tissue. With a 1 Watt laser focused to a 70 $\mu$m spot size, $P_{distance\ of\ 50\ \mu m}=25,000$ Watts/cm$^2$ (½ the power) which is insufficient to cut tissue.

In a more realistic scenario, NA=0.424, $\Delta n=0.06$, the full spread angle of the exit edge is 50°, the spot size at a distance of 50 $\mu$m is 100 $\mu$m having an area of $7.85\times10^{-5}$ cm$^2$. The power is 12,738 Watts/cm$^2$ which is insufficient to cut tissue. Thus, with a more realistic numerical aperture, the power for cutting is reduced by a factor of 4 when the exit edge is moved 50 $\mu$m away from the tissue.

In a more preferred embodiment, NA is optimized at NA=0.8 leading to a reduction of power by a factor of 10 when the exit edge is moved 50 $\mu$m away from the tissue.

The following formulas are used to calculate the exit angle $\theta_{max}$:

The critical angle $\theta_{critical}$ for effecting total internal reflection:

$$\sin \theta_{critical}=n_2/n_1$$

$$NA=\sin \theta_{max}$$

$$\sin \theta_{max}=(n_1^2-n_2^2)^{1/2}$$

In this way, the laser scalpel may simulate a razor scalpel to cut a line directly along the edge of the cutting tip while it is held in contact with the tissue, with cutting being interrupted as the scalpel is offset from the tissue or held at some distance away from the tissue. Contact cutting of the laser scalpel automatically provides tactile feedback to the surgeon not otherwise possible for a laser suspended over the tissue without contact.

Furthermore, since the waveguide 18 is a thin, flat ribbon, the cross-section of the waveguide's outlet edge defining the cutting tip 20 is straight which permits the laser beam 24 to be emitted along the full height of the cutting tip for automatically cutting along a straight line instead of a single spot.

As shown in FIG. 2, the cutting tip 20 is preferably blunt with a flat face across the width of the waveguide for providing a blunt surface which contacts the tissue being cut during operation. The blunt tip itself is preferably dull and merely supports the scalpel atop the tissue for providing tactile feedback to the surgeon, with actual cutting being effected by the laser beam emitted from the tip and concentrated in energy at the tip.

The cutting tip 20 is preferably relatively thin and flat in the width direction along the full height of the tip for emitting the laser beam along a single line for effecting straight cuts. Alternatively, the tip may be arcuate across its width, either convex or concave.

As shown in FIG. 2, the cutting tip 20 is preferably arcuate along its height to effect a convex curved contour similar to a razor scalpel for permitting similar cutting at any point along the curvature of the cutting tip. The laser beam emitted from the cutting tip will cut at any point where the tip contacts the tissue along any portion of the cutting tip or along its entire height.

The scalpel illustrated in FIG. 1 may have an outward appearance and feel like a typical razor scalpel and may be similarly used for cutting a surface such as tissue during surgery. During operation, the laser beam 24 is suitably projected from the laser 26 via, for example, an optical fiber 30. The laser beam 24 then travels through the waveguide 18 of the scalpel and out the cutting tip 20. The scalpel is manually held by a surgeon who slides the cutting tip 20 along the surface of the tissue 12 in contact therewith for laser cutting the surface.

A particular advantage of the laser scalpel illustrated in FIG. 1 is that it may be constructed of relatively inexpensive components such as plastics and silicone, for example, so that after surgery, ie. a single cutting use thereof, the scalpel 10, itself, may be simply discarded or disposed of without being reused. In an alternate embodiment, the scalpel may be made of suitable material for permitting the sterilization thereof and therefore may have the ability to be re-used multiple times as desired.

In the exemplary embodiment illustrated in FIGS. 1 and 2, the laser beam 24 is projected through the waveguide 18 in a continuous fan beam along the full height of the cutting tip 20. The ribbon form of the waveguide permits the laser beam to be emitted from the cutting tip in a continuous line as opposed to a single spot. The emitted laser line is preferably configured to have suitable power density along its full cutting height for cutting the tissue placed in contact therewith. Concentrating the laser energy along the full height of the cutting tip 20 may be accomplished in various manners.

In the exemplary embodiment illustrated in FIG. 1, the ribbon waveguide 18 extends through the shaft 14 and has a common height A over substantially its entire length. The inlet 22 of the waveguide is preferably rectangular in configuration for receiving the laser beam over its full area.

The shaft 14 preferably includes a suitable coupling or fitting 28 at its proximal end for optically coupling an optical fiber 30 from the laser 26 to the waveguide inlet. The laser 26 may be a solid-state laser which emits a laser beam in rectangular pattern. The optical fiber 30 may have a ribbon waveguide extending therethrough with a rectangular configuration corresponding to that of the laser and its beam. Alternatively, the laser beam emitted from the laser may have a circular pattern and the optical fiber may have either a circular or corresponding rectangular pattern.

The inlet 22 of the scalpel may have the same rectangular configuration as the waveguide in the fiber 30 for directly receiving the laser beam therefrom. The fitting 28 may be in the form of a simple cylindrical socket in which the complementary plug-end of the fiber 30 is inserted for mechanical and optical coupling. If desired, a suitable optical grease may be used to improve the coupling efficiency between the fiber and scalpel inlet.

Since the emitting diode of the solid-state laser 26 may be relatively large, the waveguide 18 in the scalpel itself may initially match the rectangular configuration of the diode and the waveguide in the fiber 30, but then preferably decreases in width between the inlet 22 and the outlet of the cutting tip 20 of the scalpel for concentrating the power density of the laser beam at the tip. This may be accomplished by incorporating an integral converging waist 18c in the waveguide illustrated in FIG. 1 wherein the nominal width C of the waveguide decreases to the final width B at the cutting tip.

The waist 18c may simply include converging sidewalls of the waveguide transitioning from the maximum width C which may be about 0.25 mm or 250 microns to the minimum width B which may be about 50 microns. The laser beam is thusly concentrated in power density across the width B of the cutting tip, with similarly high power density along the full height A of the cutting tip.

Illustrated in FIG. 3 is the laser scalpel 10 configured for use in an alternate embodiment in which an optical fiber 32 receives from a suitable laser 26 a laser beam in spot form instead of rectangular form. The optical fiber 32 has a cylindrical central optical core through which the laser beam is channeled to the scalpel.

Figure 4:
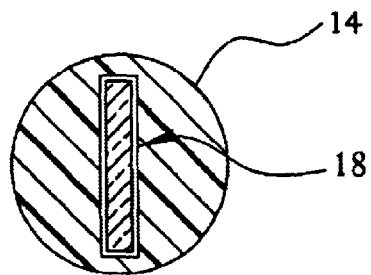
FIG. 4 is a transverse sectional view of the laser scalpel illustrated in FIG. 3 taken along line 4—4.

In this embodiment, the laser scalpel further includes an optical coupling 34 suitably disposed at the proximal end of the shaft for optically coupling the fiber 32 to the waveguide 18 of the scalpel, as illustrated in sectional view in FIG. 4.

The coupling 34 may have any conventional form including a focusing lens 34a which focuses the laser beam from the fiber 32 onto a collimating lens 34b optically aligned therewith.

The laser scalpel illustrated in FIG. 3 also includes a suitable scanner 36 optically aligned between the coupling 34 and the waveguide 18 for scanning or oscillating the laser beam along the height of the cutting tip 20.

In this way, the coupling 34 is effective for collimating and focusing the laser beam at a focused spot at the cutting tip 20 for maximum power density thereat, and then that focus spot is scanned along the height of the cutting tip to raster the beam in a single column along the tip height to automatically trace a cutting line over the full extent of the cutting tip. The laser beam may thusly be concentrated at a single spot at the cutting tip 20 and then oscillated along the cutting tip for cutting a line therealong.

The scanner 36 illustrated schematically in FIG. 3 may have various forms such as an acousto-optic scanner 36a of conventional design in which a piezoelectric crystal is energized for deflecting and scanning the laser beam through the waveguide 18 of the laser scalpel.

Figure 5:
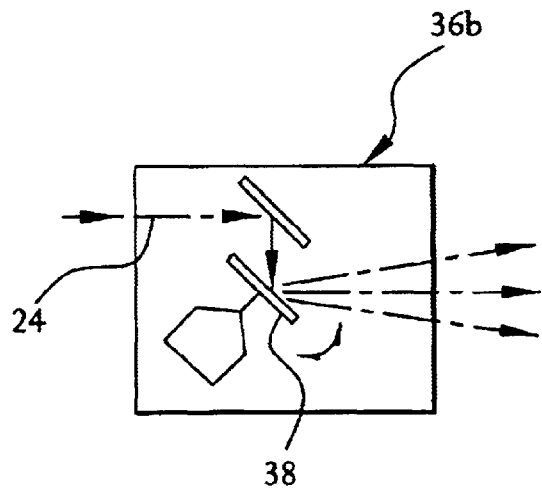
FIG. 5 is a schematic view of a laser scanner for the laser scalpel illustrated in FIG. 3 in accordance with an exemplary embodiment.

Also illustrated schematically in FIG. 3, and in more detail in FIG. 5, is an embodiment of the scanner 36 in the form of a resonating optical chopper 36b which is commercially available for other uses. The chopper 36b includes a micromirror 38 whose tilt angle may be automatically varied for reflecting the laser beam therefrom at different angles to fan the laser beam through the waveguide of the laser scalpel.

In the various embodiments disclosed above, a relatively simple laser scalpel having a ribbon waveguide therein provides a slender and narrow cutting tip 20 from which the laser beam may be emitted along a line for laser cutting thereat. The laser beam may be emitted in a continuous fan beam over the entire surface area of the cutting tip, or may be rastered in spot form along the height of the cutting tip.

In either embodiment, the laser beam is concentrated and focused at the exit edge of the cutting tip 20 where it has maximum cutting or burning power density, which quickly degrades if the cutting tip 20 is removed and spaced away from the tissue being cut.

The laser scalpel permits the surgeon to contact the cutting tip with the tissue being cut for tactile feedback, with cutting being effected substantially only when the tip contacts the tissue surface. The straight-line form of the cutting tip due to the ribbon waveguide permits straight-line cutting to be effected in a manner similar to a conventional razor scalpel. And, since cutting occurs substantially only when the cutting tip is in contact with the tissue, the depth of cutting may be accurately controlled by the direct placement of the cutting tip on the surface of the tissue to be cut as determined by the surgeon.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Figure 7:
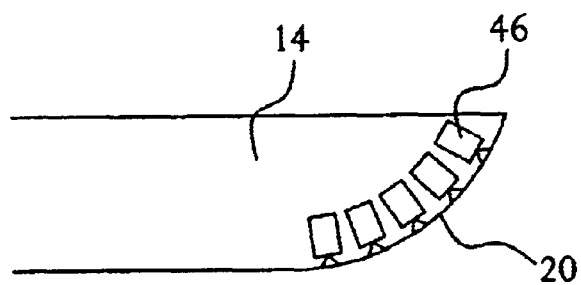
FIG. 7 is a schematic side view of a laser scalpel having a plurality of miniature lasers at the cutting tip in accordance with another embodiment of the present invention.

For example, instead of providing the laser light remotely to the scalpel from a distant laser via optical fibers 30, 32 (see FIGS. 1 and 3, respectively), the scalpel can alternatively be constructed with miniature lasers provided at or near the exit edge of the cutting tip 20 as shown in FIG. 7. Preferably, these miniature lasers 46 would each be connected to a suitable power source (e.g. power outlet, electrical generator, battery, etc.) via electrical wires (not shown). This particular construction would eliminate the need for the optical fibers 30, 32, the corresponding coupling or fitting 28 (FIG. 1) or coupling 34 (FIG. 3), and optionally, the planar optical waveguide 18. When employing the optional planar optical waveguide 18, the electrical wires and/or the miniature lasers 46 may be embedded within the waveguide 18 itself. A suitable controller connected to each miniature laser 46 may additionally be provided to control the rastering or scanning of the laser beam if desired.

Another exemplary modification which may be employed is providing the exit edge of the cutting tip 20 with a concave shape along the width of the tip 20. The concave shape would result in the laser beam diverging at a greater rate. Alternatively, the exit edge of the cutting tip 20 may be provided with a convex shape along the width of the tip 20. The convex shape would result in the laser beam diverging at a lesser rate.

Accordingly, what is desired to be secured by Letters Patent of the United States is the invention as defined and differentiated in the following claims in which I claim:

1. A laser scalpel comprising a shaft having an optical waveguide extending therethrough, said waveguide terminating at an optical cutting tip for emitting a laser beam;
   wherein said shaft includes a central longitudinal axis, said tip has a height and a width, said height and said width transverse to said axis, said scalpel emitting said laser beam from said tip along said tip height; and
   wherein said waveguide extends longitudinally through said shaft between opposite proximal and distal ends, with said tip being disposed as said distal end, said waveguide further including an inlet disposed at said proximal end for receiving said laser beam, and wherein said waveguide decreases in width from said inlet to said tip.

2. A scalpel according to claim 1 wherein said tip is blunt.

3. A scalpel according to claim 1 wherein said width of said tip is constant along said height.

4. A scalpel according to claim 1 wherein said tip is arcuate along said height.

5. A scalpel according to claim 1 wherein said tip is concave along said width.

6. A scalpel according to claim 1 wherein said tip is convex along said width.

7. A scalpel according to claim 1 wherein said shaft further includes a fitting at said proximal end for optically coupling an optical fiber to said waveguide inlet for receiving said laser beam.

8. A scalpel according to claim 1 wherein the laser beam is emitted from said tip from a plurality of locations along said tip height.

9. A scalpel according to claim 1 wherein the waveguide is flexible.

10. A scalpel according to claim 1 wherein said waveguide includes a core surrounded by cladding, and wherein said cladding has a refractive index less than that of said core.

11. A laser scalpel comprising a shaft having an optical waveguide extending therethrough, said waveguide terminating at an optical cutting tip for emitting a laser beam;
    wherein said shaft includes a central longitudinal axis, said tip has a height and a width, said height and said width transverse to said axis, said scalpel emitting said laser beam from said tip along said tip height, wherein the height is approximately 5 mm, and wherein the width is approximately 50 microns.

12. A scalpel according to claim 11 wherein said waveguide includes a core surrounded by cladding, and wherein said cladding has a refractive index less than that of said core.

13. A scalpel according to claim 11 wherein said laser beam is emitted from said tip along said tip height at an intensity to effect cutting of a surface when said tip is substantially adjacent to said surface, and wherein the intensity of said laser beam is diminished as the distance from said tip to said surface is increased.

14. A laser scalpel comprising a shaft having an optical waveguide extending therethrough, said waveguide terminating at an optical cutting tip for emitting a laser beam;
    wherein said shaft includes a central longitudinal axis, said tip has a height and a width, said height and said width transverse to said axis, said scalpel emitting said laser beam from said tip along said tip height; and
    wherein said waveguide extends longitudinally through said shaft between opposite proximal and distal ends, with said tip being disposed at said distal end, said scalpel further including an optical coupling disposed at said proximal end for optically coupling an optical fiber to said waveguide for receiving said laser beam, and said scalpel further comprising a scanner optically disposed between said coupling and said waveguide for scanning said laser beam along said tip height.

15. A scalpel according to claim 14 wherein said waveguide is planar.

16. A scalpel according to claim 14 wherein said coupling comprises a focusing lens, and a collimating lens optically aligned therewith.

17. A scalpel according to claim 14 wherein said scanner comprises a resonating optical chopper.

18. A scalpel according to claim 14 wherein said scanner comprises an acousto-optic scanner.

19. A scalpel according to claim 1 or 14 wherein said waveguide extends longitudinally through said shaft between opposite proximal and distal ends, with said tip being disposed at said distal end, and said scalpel further including an optical coupling disposed at said proximal end for optically coupling an optical fiber to said waveguide for receiving said laser beam.

20. A scalpel according to claim 14 wherein said waveguide includes a core surrounded by cladding, and wherein said cladding has a refractive index less than that of said core.

21. A scalpel according to claim 14 wherein said tip is blunt.

22. A scalpel according to claim 14 wherein said width of said tip is constant along said height.

23. A scalpel according to claim 14 wherein said tip is arcuate along said height.

24. A scalpel according to claim 14 wherein said tip is concave along said width.

25. A scalpel according to claim 14 wherein said tip is convex along said width.

26. A scalpel according to claim 14 wherein the laser beam is emitted from said tip from a plurality of locations along said tip height.

27. A scalpel according to claim 14 wherein the waveguide is flexible.

28. A scalpel according to claim 14 wherein said laser beam is emitted form said tip along said tip height at an intensity to effect cutting of a surface when said tip is substantially adjacent to said surface, and wherein the intensity of said laser beam is diminished as the distance from said tip to said surface is increased.

29. A method of using a laser scalpel, said method comprising the steps of:
    providing a laser scalpel, said laser scalpel comprising a shaft having an optical waveguide extending therethrough, said waveguide terminating at an optical cutting tip;
    projecting a laser beam through said waveguide in a continuous fan beam along a height of said tip;
    emitting said laser beam from said tip along said tip height; and
    sliding said tip along a surface for cutting said surface by said beam.

30. A method according to claim 29 wherein said waveguide includes a core surrounded by cladding, and wherein said cladding has a refractive index less than that of said core.

31. A method of using a laser scalpel, said method comprising the steps of:
    providing a laser scalpel, said laser scalpel comprising a shaft having an optical waveguide extending therethrough, said waveguide terminating at an optical cutting tip;
    projecting a laser beam through said waveguide in a continuous fan beam along a height of said tip;
    simultaneously emitting said laser beam from said tip from a plurality of locations along said tip height; and
    sliding said tip along a surface for cutting said surface by said beam.

32. A method according to claim 21 wherein said waveguide includes a core surrounded by cladding, and wherein said cladding has a refractive index less than that of said core.

33. A method of using a laser scalpel, said method comprising the steps of:
    providing a laser scalpel, said laser scalpel comprising a shaft having an optical waveguide extending therethrough, said waveguide terminating at an optical cutting tip;

projecting a laser beam through said waveguide;

scanning said laser beam through said waveguide to raster said beam along a height of said tip;

emitting said laser beam from said tip along said tip height; and sliding said tip along a surface for cutting said surface by said beam.

34. A method according to claim 33 wherein said waveguide includes a core surrounded by cladding, and wherein said cladding has a refractive index less than that of said core.

35. A method according to claim 33 wherein said laser beam is emitted from said tip along said tip height at an intensity to effect cutting of said surface when said tip is substantially adjacent to said surface, and wherein the intensity of said laser beam is diminished as the distance from said tip to said surface is increased.

36. A method of using a laser scalpel, said method comprising the steps of:

providing a laser scalpel, said laser scalpel comprising a shaft having an optical waveguide extending therethrough, said waveguide terminating at an optical cutting tip;

projecting a laser beam through said waveguide;

focusing said laser beam at said cutting tip;

emitting said laser beam from said tip along a height of said tip; and sliding said tip along a surface for cutting said surface by said beam.

37. A method according to claim 36 wherein said waveguide is planar.

38. A method according to claim 36 wherein said waveguide includes a core surrounded by cladding, and wherein said cladding has a refractive index less than that of said core.

39. A method according to claim 36 wherein said laser beam is emitted from said tip along said tip height at an intensity to effect cutting of said surface when said tip is substantially adjacent to said surface, and wherein the intensity of said laser beam is diminished as the distance from said tip to said surface is increased.

40. A laser scalpel comprising an optical cutting tip having a height and a width, said scalpel further comprising a plurality of miniature lasers provided adjacent to the optical cutting tip for emitting laser beams from the tip along said tip height.

41. A scalpel according to claim 40 wherein said scalpel further comprises an optical waveguide, said waveguide terminating at said tip, wherein said plurality of miniature lasers are provided within said waveguide.

42. A scalpel according to claim 41 wherein said waveguide is planar.

43. A scalpel according to claim 41 wherein the waveguide is flexible.

44. A scalpel according to claim 41 wherein said waveguide includes a core surrounded by cladding, and wherein said cladding has a refractive index less than that of said core.

45. A scalpel according to claim 40 wherein said tip is blunt.

46. A scalpel according to claim 40 wherein said width of said tip is constant along said height.

47. A scalpel according to claim 40 wherein said tip is arcuate along said height.

48. A scalpel according to claim 40 wherein said tip is concave along said width.

49. A scalpel according to claim 40 wherein said tip is convex along said width.

50. A scalpel according to claim 40 wherein the height is approximately 5 mm, and wherein the width is approximately 50 microns.

51. A scalpel according to claim 40 wherein said plurality of miniature lasers are connected to a power source via electrical wires.

52. A scalpel according to claim 40 wherein said laser beams are emitted from said tip along said tip height at an intensity to effect cutting of a surface when said tip is substantially adjacent to said surface, and wherein the intensity of said laser beams is diminished as the distance from said tip to said surface is increased.

53. A method of using a laser scalpel, said method comprising the steps of:

providing a laser scalpel, said laser scalpel further comprising an optical cutting tip having a height and a width, said scalpel further comprising a plurality of miniature lasers provided adjacent to the optical cutting tip;

providing laser beams from said plurality of miniature lasers;

emitting said laser beams from said tip along said height of said tip; and sliding said tip along a surface for cutting said surface by said beams.

54. A method according to claim 53 wherein said scalpel further comprises an optical waveguide, said waveguide terminating at said tip, wherein said plurality of miniature lasers are provided within said waveguide.

55. A method according to claim 54 wherein said waveguide is planar.

56. A method according to claim 54 wherein said waveguide includes a core surrounded by cladding, and wherein said cladding has a refractive index less than that of said core.

57. A method according claim 53 wherein the laser beams are simultaneously emitted from said tip from a plurality of locations along said tip height.

58. A method according to claim 53 further comprising focusing said laser beams at said cutting tip.

59. A method according to claim 53 wherein said laser beams are emitted from said tip along said tip height at an intensity to effect cutting of said surface when said tip is substantially adjacent to said surface, and wherein the intensity of said laser beams is diminished as the distance from said tip to said surface is increased.

60. A laser scalpel comprising a shaft having an optical waveguide extending therethrough, said waveguide terminating at an optical cutting tip for emitting a laser beam;

wherein said shaft includes a central longitudinal axis, said tip has a height and a width, said height and said width transverse to said axis, said scalpel emitting said laser beam from said tip along said tip height, wherein said laser beam is emitted from said tip along said tip height at an intensity to effect cutting of a surface when said tip is substantially adjacent to said surface, and wherein the intensity of said laser beam is diminished as the distance from said tip to said surface is increased; and wherein said waveguide extends longitudinally through said shaft between opposite proximal and distal ends, with said tip being disposed at said distal end, said waveguide further including an inlet disposed at said proximal end for receiving said laser beam, and wherein said waveguide decreases in width from said inlet to said tip.

61. A scalpel according to claim 60 wherein said waveguide includes a core surrounded by cladding, and wherein said cladding has a refractive index less than that of said core.

62. A method of using a laser scalpel, said method comprising the steps of:

providing a laser scalpel, said laser scalpel comprising a shaft having an optical waveguide extending therethrough, said waveguide terminating at an optical cutting tip;

projecting a laser beam through said waveguide in a continuous fan beam along a height of said tip;

emitting said laser beam from said tip along said tip height; and sliding said tip along a surface for cutting said surface by said beam;

wherein said laser beam is emitted from said tip along said tip height at an intensity to effect cutting of said surface when said tip is substantially adjacent to said surface, and wherein the intensity of said laser beam is diminished as the distance from said tip to said surface is increased.

63. A method according to claim 62 wherein said waveguide includes a core surrounded by cladding, and wherein said cladding has a refractive index less than that of said core.

* * * * *